United States Patent
Retsina et al.

(10) Patent No.: US 9,453,249 B2
(45) Date of Patent: *Sep. 27, 2016

(54) PROCESS FOR PRODUCING HEMICELLULOSE SUGARS AND ENERGY FROM BIOMASS

(71) Applicant: API Intellectual Property Holdings, LLC, Atlanta, GA (US)

(72) Inventors: Theodora Retsina, Atlanta, GA (US); Vesa Pylkkanen, Atlanta, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 332 days.

This patent is subject to a terminal disclaimer.

(21) Appl. No.: 13/950,289

(22) Filed: Jul. 25, 2013

(65) Prior Publication Data

US 2013/0309728 A1    Nov. 21, 2013

Related U.S. Application Data

(63) Continuation of application No. 13/026,280, filed on Feb. 13, 2011, now Pat. No. 8,518,672, which is a continuation of application No. PCT/US2010/039481, filed on Jun. 22, 2010.

(60) Provisional application No. 61/219,759, filed on Jun. 23, 2009, provisional application No. 61/219,764, filed on Jun. 23, 2009.

(51) Int. Cl.
| | |
|---|---|
| *C12P 19/02* | (2006.01) |
| *C08B 37/00* | (2006.01) |
| *C08H 8/00* | (2010.01) |
| *C12P 19/14* | (2006.01) |
| *C13K 1/02* | (2006.01) |
| *C13K 13/00* | (2006.01) |
| *F23G 5/04* | (2006.01) |

(52) U.S. Cl.
CPC ............ *C12P 19/02* (2013.01); *C08B 37/0003* (2013.01); *C08B 37/0057* (2013.01); *C08H 8/00* (2013.01); *C12P 19/14* (2013.01); *C13K 1/02* (2013.01); *C13K 13/00* (2013.01); *F23G 5/04* (2013.01)

(58) Field of Classification Search
None
See application file for complete search history.

(56) References Cited

U.S. PATENT DOCUMENTS

| | | |
|---|---|---|
| 5,635,071 A | 6/1997 | Al-Samadi |
| 5,846,788 A | 12/1998 | Pedersen |
| 8,030,039 B1 * | 10/2011 | Retsina ................... C12P 7/06 162/1 |
| 8,518,672 B2 * | 8/2013 | Retsina et al. ............... 435/105 |
| 2007/0079944 A1 | 4/2007 | Amidon |
| 2007/0102359 A1 | 5/2007 | Lombardi |
| 2008/0182305 A1 | 7/2008 | Foody |
| 2008/0196847 A1 | 8/2008 | van Heiningen |
| 2009/0020481 A1 | 1/2009 | Bailie |

OTHER PUBLICATIONS

International Search Report for PCT/US2010/033662 (Mailed Aug. 25, 2010).

* cited by examiner

*Primary Examiner* — Hope Robinson
(74) *Attorney, Agent, or Firm* — Ryan P. O'Connor

(57) ABSTRACT

A method for the production of alcohol and other bioproducts hemicelluloses extracted from biomass prior to thermal conversion of the biomass to energy. The process can be integrated with the host plant process to minimize the energy loss from extracting hemicelluloses. Also disclosed is a Stepwise enzymatic break down of cellulose fibers from a pulping operation which is performed with the redeployment of equipment and vessels contained within typical existing pulp and paper manufacturing mills. The preferred feedstock is highly delignified pulp from acid or alkaline pulping process or from bleaching stage.

19 Claims, 3 Drawing Sheets

PROCESS FOR PRODUCING HEMICELLULOSE SUGARS AND ENERGY FROM BIOMASS

This patent application is a continuation of U.S. Pat. No. 8,518,672, issued on Aug. 27, 2013, which in turn is a continuation of patent application PCT/US2010/039481, filed Jun. 22, 2010, which claims priority to provisional applications U.S. Patent App. Nos. 61/219,759 and 61/219,764 each filed Jun. 23, 2009. All of these applications are hereby incorporated by reference herein.

FIELD OF THE INVENTION

This invention relates, in general, to the extraction of hemicelluloses from biomass prior to thermal conversion of the biomass to energy and the treatment of the extracted hemicelluloses for the production of alcohol and other bioproducts. The invention also relates to this invention relates, in general to the enzymatic conversion of cellulosic fiber to glucose and other monomeric sugars and specifically the re-utilization of existing process equipment in pulp and paper mills

BRIEF DESCRIPTION OF THE DRAWINGS

A more complete understanding of the present invention may be obtained by reference to the following detailed description when read in conjunction with the accompanying drawings wherein.

Figure 1:
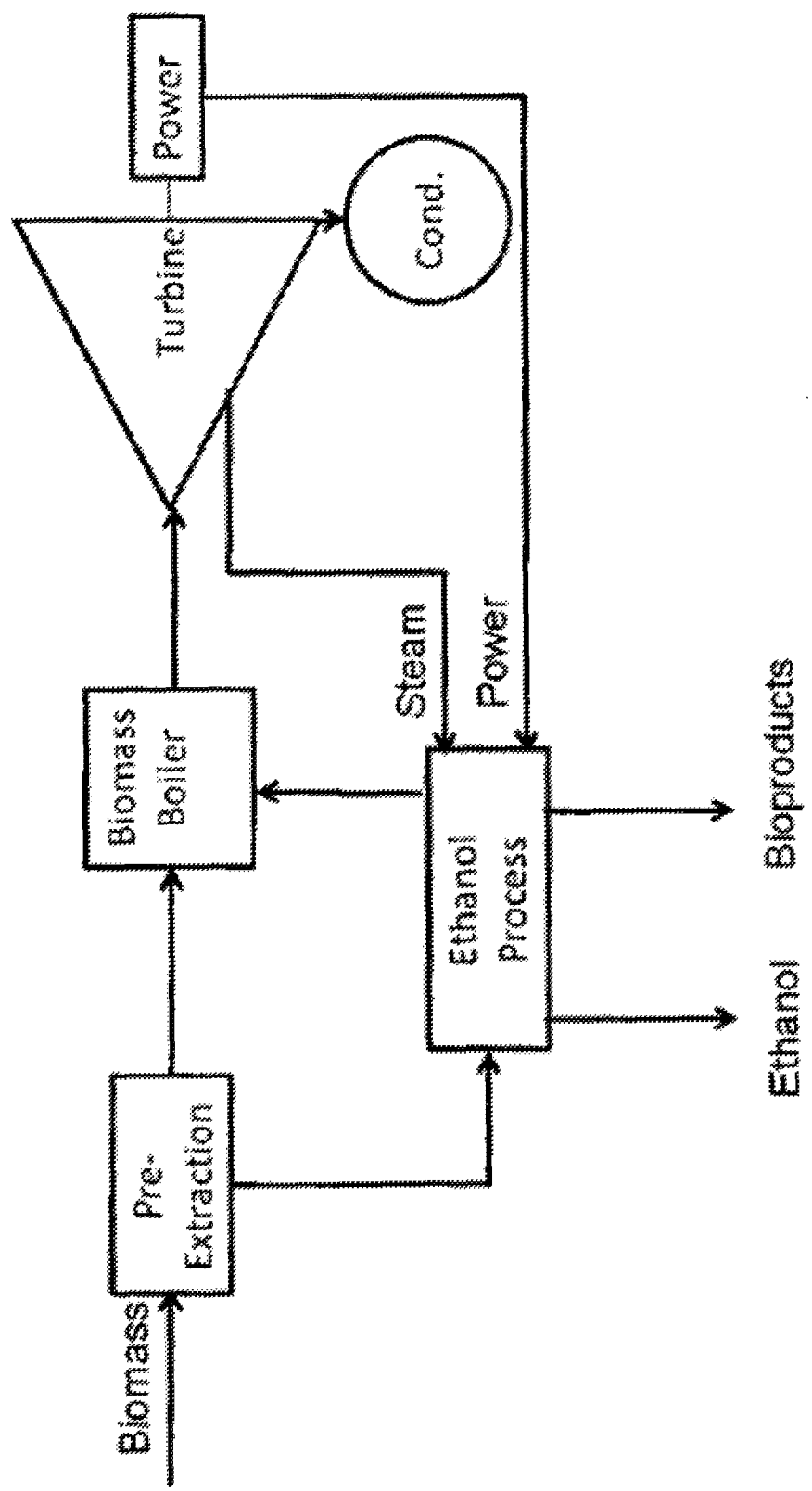
FIG. 1. illustrates a conceptual flow sheet example of an embodiment of the invention process.

Note: The method steps illustrated in the figures are preferred embodiments and not intended to restrict the scope of the invention. The invention may be practiced with fewer or addition steps in any plausible combination even if not shown in the drawings or in the detailed description.

BACKGROUND OF THE INVENTION

Renewable energy generation from forest residues is commonly practiced in the forest products industries. The U.S. forest products industry consumed 27.1 million tons of wood derived biomassin the generation of steam. By comparison, the power generation industry used 11.9 million tons of biomass of which 80% is wood derived. The biomass consumption in energy and power generation is expected to double in every 10 years until 2030.

The major components of cellulosic biomass are lignin, hemicelluloses and cellulose. The forest products industry practices the addition of steam to wood chips, to dissolve predominantly hemicelluloses at temperatures above 160 degrees C.; this process is termed "steam explosion". Hemicelluloses removed in this process is termed "extract". A concentration of the extract through evaporation is energy intensive, although it is currently practiced in industry to produce molasses.

Previous research indicates that ethanol, acetic acid and their byproducts can be derived from the extract. Hardwood in particular, and softwood to a lesser extent produces an extract rich in acetic acid and sugars as taught by Amidon et al. in (U.S. Patent Application No. 2007/0079944 A1, Apr. 12, 2007).

The present inventors found, inter alia, an alternative method to extract hemicelluloses from biomass prior to thermal conversion of the biomass to energy and have developed a process wherein the hemicelluloses in the extract can be converted to alcohol and other chemical bioproducts in an energy efficient process.

In a further embodiment, there is disclosed enzymatic conversion of cellulosic fiber to glucose and other monomeric sugars and specifically the re-utilization of existing process equipment in pulp and paper mills.

The current practice in proposed cellulosic ethanol processes is to add enzymes to 6-15% solids cellulosic fiber stock, termed medium consistency stock, and wait for completion of cellulose hydrolysis in 24-72 hours. This process is inefficient, because mixing of medium consistency stock consumes disproportionally more energy than mixing of low consistency (1-6% solids) stock. However, the equipment required for the storage and processing of low consistency stock are larger than for medium or high consistency (16-35% solids) stock.

The activity of the enzymes reduces upon time, because of binding to non-specific sites, e.g., lignin. Mixing at high consistency is not efficient and slows enzymatic reaction. Over the hydrolysis period, the stock consistency decreases thus improving both mixing efficiency and enzyme activity, however high dissolved sugar concentration from the hydrolyzed cellulose fiber has a negative impact on enzyme activity.

Jameel et al. have taught in U.S. patent application "HIGH CONSISTENCY ENZYMATIC HYDROLYSIS FOR THE PRODUCTION OF ETHANOL"a method of converting biomass to sugars using two step process, where enzymes are adsorbed on biomass at approximately 5% consistency for 5-10 minutes and then dewatered to 20-30% consistency for 24-48 hours. Jameel et al. further taught that these steps can be repeated and the filtrate recycled to the previous step.

The current inventors have discovered, inter alia, that a stepwise addition of enzymes improved the hydrolysis yields at lower enzyme dosage and at low consistency typical of the stock consistencies used in pulp and paper mills. This advantageous because existing pulp and paper mill equipment and vessel infrastructure can be redeployed.

SUMMARY OF THE INVENTION

The present invention describes a process for the extraction of hemicelluloses from biomass by steam explosion prior to thermal conversion of the biomass to energy and the treatment of the extracted hemicelluloses through hydrolysis, evaporation, fermentation and distillation steps to recover and concentrate alcohol, acetate, and other chemical bioproducts. The process is integrated with the host biomass thermal energy plant and/or host facility to minimize process energy and water consumption. Also disclosed is a biorefinery process to extract hemicelluloses from cellulosic biomass destined for thermal conversion to energy, while maintaining full cellulose material utilization. The process may use steam for extraction of the hemicelluloses. The process my further include steam extraction pressure at between 5 and 30 atmospheres and/or where the steam extraction time is between 2 minutes and 1 hour. The process may also include evaporation for the concentration of the hemicelluloses containing extract up to 25% or more. The process may also include the use of mechanical vapor recompression evaporation for said evaporation. The process may also include having extract maintained below acetic acid dissociation point of pH 4.8 to remove acetic acid by evaporation. The process may also include using stillage from distillation bottoms as biomass for thermal conversion to energy. The process may also include using a host facility steam generator feed water heated with waste heat from the biorefinery process. The process may also include a biorefinery process integrated with a host facility to minimize overall steam and water. The process may also include using steam and acetic acid for extraction of the hemicelluloses and/or where steam and sulfur dioxide is used for extraction of the hemicelluloses and or where steam and a mineral acid is used for extraction of the hemicelluloses. The process may also include using a biorefinery process comprising an extraction reactor, washing, low solids evaporation, hydrolysis, post hydrolysis evaporation, fermentation, distillation, product drying, distillation. product drying, and solid biomass dewatering. The process may also include using mechanical vapor recompression evaporators for said evaporation.

To summarize the alternate embodiment relating to enzymatic conversion of cellulosic fiber to glucose and other monomeric sugars, there is disclosed a process which proposes that a stepwise enzymatic break down of cellulose fibers from a pulping operation is performed using the equipment and vessels contained within typical pulp and paper manufacturing facilities. The preferred cellulose fiber feedstock to an enzymatic hydrolysis process is highly delignified pulp from an acid or alkaline pulping process, or bleaching process. Cellulase enzymes are used to break down the cellulose fibers to glucose and hemicellulases are used to free hemicelluloses side chains. These enzymes are added stepwise to the pulp suspension. High efficiency mixing vessels termed pulpers are used to disperse and adsorb the enzymes on cellulose fibers at a pulp consistency of 3-12% solids. After short adsorption time, the pulp suspension is transferred to agitated vessels which are used for retention storage during the hydrolysis. At specified times, additional enzymes are added in one or more steps to boost the hydrolysis to completion. Hydrolyzed glucose may be filtered and the remaining pulp suspension may be concentrated or diluted in between the enzyme additions.

Also disclosed in the second embodiment is a process using stepwise addition of enzymes and pulp for the enzymatic hydrolysis of cellulose fiber. The process further includes pulp being added stepwise to maintain optimum consistency for mixing and enzymatic activity. The process further includes enzyme being added stepwise to maintain hydrolysis activity during the extended period. The process further includes dissolved sugars being removed to reduce enzymatic inhibition. The process further includes utilizing existing pulp and paper mill equipment in enzymatic hydrolysis of cellulose fibers. The process further includes pulp and paper machine pulpers being used to promote enzymes contacting cellulose fibers. The process further includes pulp and paper machine stock chests being used for retention storage to provide enzyme reaction time. The process further includes pulp and paper machine saveall filters being used for dewatering of a pulp suspension. The process further includes pulp and paper machine fourdrinier sections being used for dewatering of unhydrolyzed solids.

The above summary is not a limitation of the scope of the invention which are defined by the claims and supported by the entire patent application document.

DETAILED DESCRIPTION OF THE INVENTION

Figure 2:
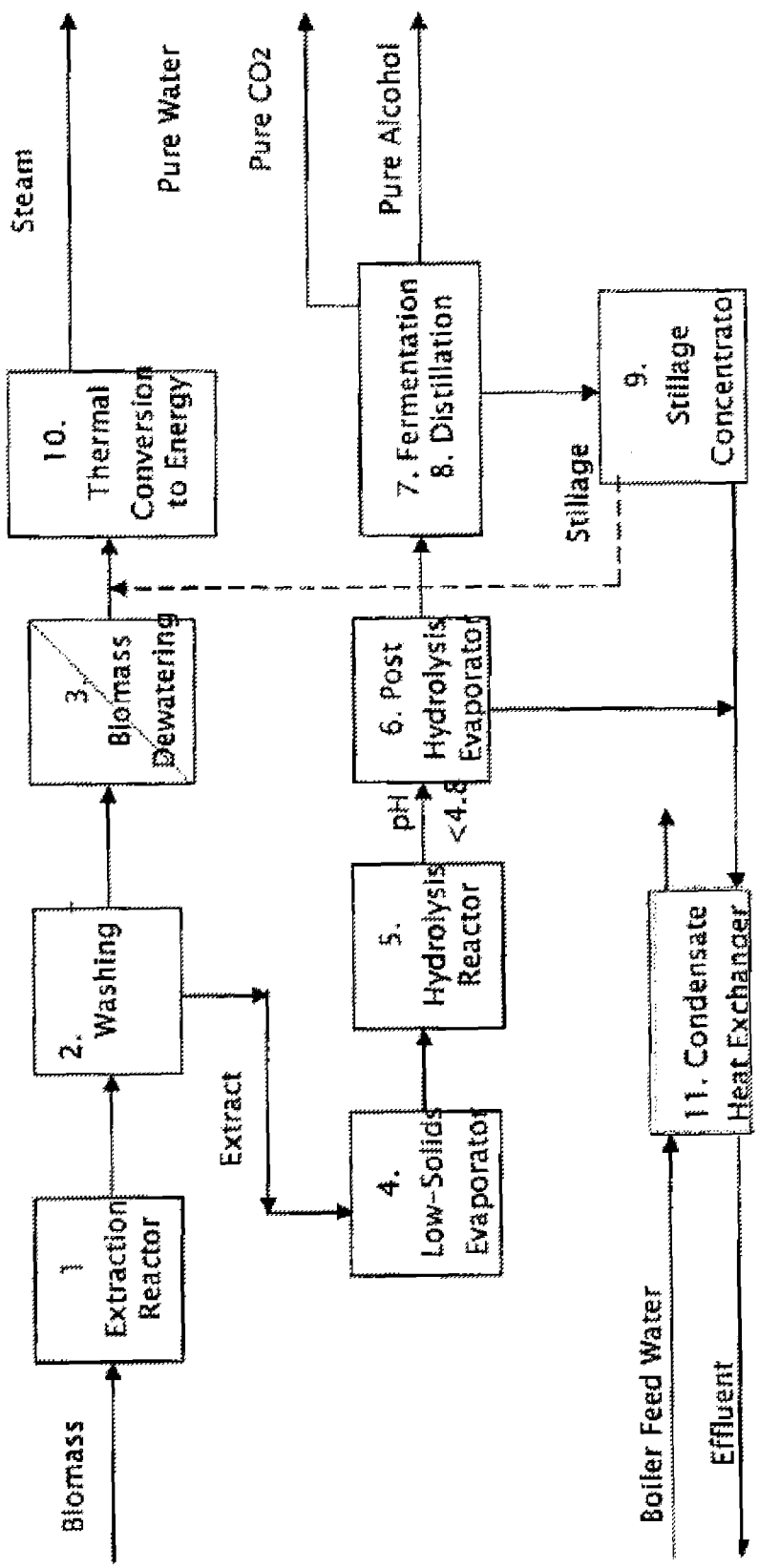
FIG. 2. illustrates a flow sheet example of an embodiment of the invention process steps.

Reference should be had to FIGS. 1 and 2 which include legends which correspond to the description below.

The following steps may be taken in any order plausible and steps may be omitted and still conform to the invention.

The First Step of the Process is Extraction. Cellulosic biomass is charged into a batch or continuous extraction reactor vessel and steam is added to heat the biomass at a pressure of 5-30 atmospheres for a duration of 2 minutes or more to obtain 10-30% yield of dissolved solids comprised mostly of hemicelluloses and lignin. This extraction process is termed steam explosion. The reaction is catalyzed by formation of acetic acid from the cellulosic biomass. Additional catalyst, such as acetic acid or a mineral acid or sulfur dioxide may be used to increase the dissolved solids fraction or to speed the extraction process.

The Second Step of the Process is Washing. Following extraction by steam explosion, the heated biomass is washed with water, and/or recirculated wash filtrate, and drained to recover the majority of the dissolved cellulosic biomass components. The wash filtrate, termed extract, contains dissolved xylan, glucan, mannan, arbinan, galactan and acetyl groups in oligomeric form of hemicelluloses as well as lignin. The extract has a low organic solids concentration of 1%-12% by weight. The majority of the water in the extract must be removed before an economic treatment of hemicelluloses is possible.

The Third Step of the Process is Dewatering of the Biomass. The remaining solid biomass is dewatered to approximately the same moisture content that it was when fed to the extraction reactor, typically 40%-60% solids, by pressing it to approximately 30 atmospheres or more mechanical pressure through a commercial plug screw feeder, other pressing device, or other thermal/mechanical dewatering device. The host facility therefore experiences little or no change in the moisture content of its biomass feedstock available to be fed to the existing equipment for thermal conversion to energy.

The fourth step of the process is low solids evaporation. Evaporation is used to concentrate the low solids extract from the second step, in-reactor washing, from 1-5% solids to around 25% or more. This concentration is preferably performed using a mechanical vapor recompression evaporator which is suitable because the boiling point rise of the extract is small. Evaporated vapor is compressed, and condensed in the hot side of the evaporator to produce an almost equivalent amount of evaporation. If the extract feed concentration is over 5% solids, this step may be omitted. When the pH of this step is kept below the acetic acid dissociation point of pH 4.8, acetic acid in the extract, a fermentation inhibitor, is volatilized to the vapor fraction.

The Fifth Step of the Process is Hydrolysis. Concentrated extract from the low solids evaporation is hydrolyzed using sulfuric acid, heat or enzymes. Oligomer hemicelluloses in the concentrated extract are converted into monomer sugars and acetyl groups are released. The hydrolyzate resulting from the hydrolysis is controlled to pH 3-4.8 to maintain acetic acid in unassociated form.

The Sixth Step of the Process is Post Hydrolysis Evaporation. Hydrolyzate from hydrolysis is concentrated up to 50% solids by evaporation, preferably using a mechanical vapor recompression evaporator. More of the remaining acetic acid and water is evaporated in this step. Under the appropriate economic criteria, this step could be done with steam evaporation.

The Seventh Step of the Process is Fermentation of Sugars. Sugars in the concentrated hydrolyzate are fermented in a continuous or batch fermentation tanks with one or more micro-organisms capable of converting five and six carbon sugars into alcohol and carbon dioxide. The majority of acetic acid, which may inhibit fermentation, was removed in the previous evaporation step. Some additional acetic acid may be formed during fermentation. Nutrients and pH adjustment chemicals as well as make-up fermentative organism are added in this fermentation step as and if needed. Carbon dioxide is removed from the fermenters and scrubbed with cool water for alcohol recovery. This purified gas can be further compressed and sold as industrial grade carbon dioxide. The fermentation broth, commonly termed "beer", from the fermentation step is sent to a distillation column.

The Eighth Step of the Process is Distillation of Ethanol. The beer from the fermentation step is sent to a beer distillation column to separate the alcohol from the solids and residual sugars. Alcohol leaving as the overhead from the distillation column is recovered at approximately 30-50 mass-% strength. The final concentration of the alcohol product is performed in a rectifying column and drying system, preferably a molecular sieve, to obtain over 99-mass % alcohol.

The Ninth Step of the Process is the Solids Concentration from the Stillage. The solids, commonly termed "stillage", from the beer distillation column bottom can be further evaporated in an optional concentrator, preferably a mechanical vapor recompression concentrator to achieve zero-liquid discharge operation.

The Tenth Step of the Process is Combustion of Biomass. The dewatered biomass from the third step and the concentrated stillage from the ninth step are fed to the host facility existing equipment for thermal conversion to energy The Eleventh Step of the Process is the Integration of the Biorefinery with the Existing Host Facility. The physical plant combining the process steps as a whole or in part to produce alcohol and other chemical bioproducts is termed "biorefinery".

An energy integration analysis of the proposed biorefinery process indicates that utilizing mechanical vapor recompression evaporators achieves the minimum need for cooling water. The waste heat generated in the process is absorbed into the evaporator and column condensate streams, which can be utilized in the host facility to minimize overall steam and water consumption, and is preferably used for steam generator feedwater heating.

Figure 3:
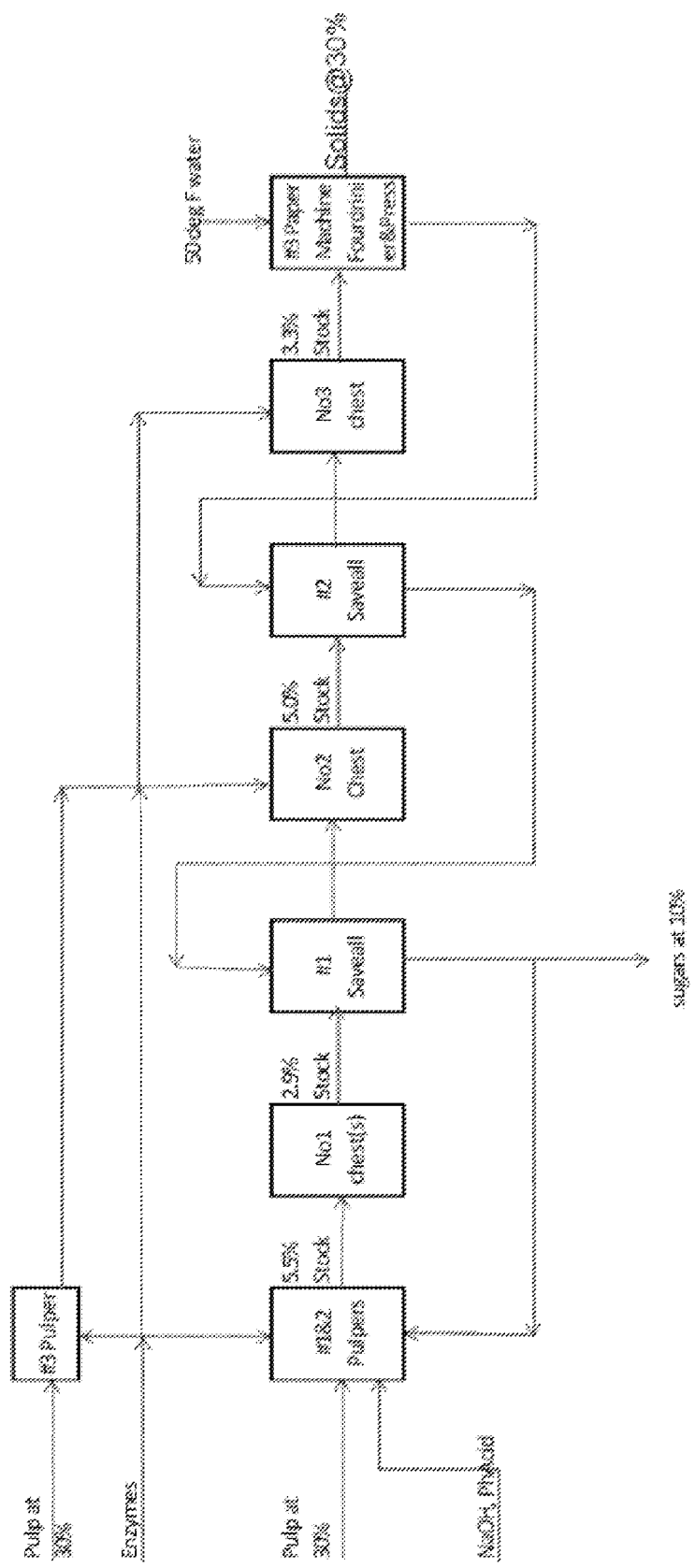
FIG. 3. illustrate a flow sheet of a further embodiment of the invention relating to enzymatic conversion of cellulosic fiber.

In the second embodiment related to enzymatic conversion of cellulosic fiber to glucose and other monomeric sugars, the detailed description is as follows. Reference should be had to FIG. 3 which include legends which correspond to the description below.

The first step of the process is the pulp mixing at 3-10% consistency, using a low dosage of enzymes. The cellulose fiber feedstock, termed pulp, is prepared by chemical pulping of wood chips in acidic or alkaline conditions and may be partially bleached to have residual lignin content below 3% by weight of the feedstock. The pulp at a consistency of 3%-10% solids is mixed with an enzyme formulation which is preferably at less than 3% by weight in proportion to cellulose and hemicellulose content of the delignified pulp. Mechanical mixing is performed to promote enzymes contacting the cellulose fibers. Mixing tanks in existing pulp and paper mills include broke and stock pulpers these are among the existing equipment and vessels that can be redeployed for this purpose.

The Second Step of the Process is the Retention of Pulp Suspension, while Maintaining Moderate Mixing. Following step 1, retention time must be provided to achieve the desired enzyme reaction on the pulp stock to produce a partially hydrolyzed pulp suspension. Retention tanks in existing pulp and paper mills include high density storage, low density storage, machine chests, bleach towers, and broke surge tanks; these are the among the existing equipment and vessels that can be redeployed for this purpose.

The Third Step of the Process is an Addition of a Small Amount of Enzymes. On reaching 25-50% dissolution of sugars, as measured by pulp weight loss, the partially hydrolyzed pulp suspension from the second step may be dewatered back to 3-10% consistency, without significant loss of adsorbed enzymes. Dissolved sugars in the filtrate are removed to reduce enzymatic inhibition. Filtrate from subsequent steps may also be used to wash the pulp in the dewatering process. A small amount of enzyme formulation used in the first step is then added to the dewatered pulp suspension to maintain hydrolysis activity during the extended period. New pulp from the first step is also added as needed to maintain optimum consistency for mixing and enzymatic activity. Dewatering devices in existing pulp and paper mills include side hill screens, stock washers, savealls, fourdrinier wire sections and press sections of pulp and paper machines; these are the among the existing equipment and vessels that can be redeployed for this purpose.

The second and third steps may be repeated one or more times to achieve complete hydrolysis.

The Final Step of the Process is to Remove Unhydrolyzed Solids, Consisting Mainly Lignin in the Pulp Feedstock. The lignin is filtered from the sugar solution. The filter cake may be washed and pressed to minimize the sugar content. The lignin filtering devices in existing pulp and paper mills include stock washers, screw presses, fourdrinier wire sections and press sections of pulp and paper machines; these are among the existing equipment and vessels that can be redeployed for this purpose.

EXAMPLES

Example 1

5 grams of O.D. pine pulp at 18.5% consistency from alcohol sulfite process was dissolved with deionized water to 100 ml of pulp suspension. 250 mL Erlenmeyer flasks were used. Enzyme stock solution was prepared in 50 mM acetate buffer (pH 5.02). Final volume was made up to 100 mL with deionized water. 100 mg of Novozymes Ctec/Htec enzymes were added at [8:1] ratio. Enzymatic reaction was incubated on a water bath at 50° C. and mixed at 200 rpm.

After the first 36 hour retention period, 25 mg of enzyme formulation was added. The hydrolysis was allowed to proceed another 36 hours, at which point another 25 mg of enzyme was added.

The procedure resulted 84.7% weight loss. In comparison, the hydrolysis of same pulp with the same 150 mg enzyme dosage in one step resulted 84% weight loss.

Example 2

5 grams of O.D. pine pulp at 18.5% consistency from alcohol sulfite process was dissolved with deionized water to 100 ml of pulp suspension. 250 mL Erlenmeyer flasks were used. Enzyme stock solution was prepared in 50 mM acetate buffer (pH 5.02). Final volume was made up to 100 mL with deionized water. 50 mg of Novozymes Ctec/Htec enzymes were added at [8:1] ratio. Enzymatic reaction was incubated on a water bath at 50° C. and mixed at 200 rpm.

After 36 hours, 50 mg of enzyme formulation was added. The hydrolysis was allowed to proceed another 36 hours, at which point another 50 mg of enzyme was added.

The procedure resulted to 75.7% weight loss. In comparison, the hydrolysis of same pulp with the same 150 mg enzyme dosage in one step resulted 84% weight loss.

Example 3

5 grams of O.D. pine pulp at 18.5% consistency from alcohol sulfite process was dissolved with deionized water to 100 ml of pulp suspension. 250 mL Erlenmeyer flasks were used. Enzyme stock solution was prepared in 50 mM acetate buffer (pH 5.02). Final volume was made up to 100 mL with deionized water. 100 mg of Novozymes Ctec/Htec enzymes were added at [8:1] ratio. Enzymatic reaction was incubated on a water bath at 50° C. and mixed at 200 rpm for 12 hours.

The suspension was dewatered to 10% consistency. The hydrolysis proceeded to approximately 32% weight loss in 24 hours. A fresh buffer and 25 mg of enzyme formulation was added to 5% consistency. The hydrolysis was allowed to proceed another 12 hours, at which point the consistency was increased to 10% for 24 hours.

The hydrolysis proceeded to approximately 47% weight loss, at which point fresh buffer and 25 mg of enzyme formulation was added to 5% consistency. The hydrolysis was allowed to proceed another 12 hours, at which point the consistency was increased to 10% for 24 hours.

The procedure resulted to 84.8% weight loss. In comparison, the hydrolysis of same pulp with the same 150 mg enzyme dosage in on step resulted 84% weight loss.

What is claimed is:

1. A process for producing hemicellulose sugars from cellulosic biomass, said process comprising:
    (a) extracting hemicelluloses from cellulosic biomass by a batch or continuous extraction reactor in the presence of steam, to produce a cellulose-rich solids stream and a liquid extract comprising water, wherein hemicelluloses and acetyl groups are released from said cellulosic biomass, and wherein said liquid extract contains at least 5 wt % solids;
    (b) hydrolyzing said liquid extract in the presence of sulfuric acid, heat, or enzymes, to produce a hydrolyzate comprising hemicellulose sugars and additional acetyl groups released during said hydrolyzing said liquid extract;
    (c) introducing said hydrolyzate to an evaporation stage, to produce a concentrated extract, wherein said evaporation stage is operated at a pH of 4.8 or less, wherein acetic acid obtained from said acetyl groups released from said cellulosic biomass and said additional acetyl groups released during said hydrolyzing said liquid extract, is evaporated from said evaporation stage, and wherein said concentrated extract comprises said hemicellulose sugars; and
    (d) recovering or further processing said hemicellulose sugars.

2. The process of claim 1, wherein said extracting in step (a) utilizes a mineral acid.

3. The process of claim 1, wherein said extracting in step (a) utilizes acetic acid.

4. The process of claim 1, wherein said extracting in step (a) utilizes sulfur dioxide.

5. The process of claim 1, comprising a step of washing said cellulose-rich solids stream to produce said liquid extract.

6. The process of claim 1, wherein mechanical-vapor recompression is employed for said evaporation stage.

7. The process of claim 1, wherein said evaporation stage is controlled at a pH selected from 3 to 4.8.

8. The process of claim 1, said process further comprising dewatering said cellulose-rich solids stream from step (a), to produce dewatered solids; and combusting said dewatered solids, to produce energy.

9. A process for producing hemicellulose sugars from cellulosic biomass, said process comprising:
    (a) extracting hemicelluloses from cellulosic biomass with water and heat to produce a cellulose-rich solids stream and a liquid extract comprising said water, wherein said hemicelluloses and acetyl groups are released from said cellulosic biomass;
    (b) concentrating said liquid extract in a first evaporation stage that removes a majority of said water from said liquid extract, to produce a low-solids extract, wherein said first evaporation stage is operated at a pH of 4.8 or less, and wherein a first amount of acetic acid, is obtained from said acetyl groups released from said cellulosic biomass, is evaporated from said first evaporation stage;
    (c) hydrolyzing said low-solids extract from step (b) in the presence of sulfuric acid, heat, or hemicellulase enzymes, to produce a hydrolyzate comprising hemicellulose sugars and additional acetyl groups released during said hydrolyzing said low-solids extract;
    (d) introducing said hydrolyzate to a second evaporation stage, to produce a concentrated extract, wherein said second evaporation stage is operated at a pH of 4.8 or less, wherein a second amount of acetic acid obtained from said acetyl groups released during said hydrolyzing said low-solids extract, is evaporated from said second evaporation stage, and wherein said concentrated extract comprises said hemicellulose sugars; and
    (e) recovering or further processing said hemicellulose sugars.

10. The process of claim 9, wherein said extracting in step (a) utilizes a mineral acid.

11. The process of claim 9, wherein said extracting in step (a) utilizes acetic acid.

12. The process of claim 9, wherein said extracting in step (a) utilizes sulfur dioxide.

13. The process of claim 9, comprising a step of washing said cellulose-rich solids stream to produce said liquid extract.

14. The process of claim 9, wherein mechanical-vapor recompression is employed for said first evaporation stage, said second evaporation stage, or both of these evaporation stages.

15. The process of claim 9, wherein said second evaporation stage is controlled at a pH selected from 3 to 4.8.

16. The process of claim 9, wherein said first evaporation stage is operated to produce a low-solids extract with a solids concentration up to about 25 wt %.

17. The process of claim 9, wherein said second evaporation stage is operated to produce a concentrated extract with a solids concentration up to about 50 wt %.

18. The process of claim 9, said process further comprising dewatering said cellulose-rich solids stream from step (a), to produce dewatered solids; and combusting said dewatered solids, to produce energy.

19. A process for producing hemicellulose sugars from cellulosic biomass, said process comprising:
   (a) extracting hemicelluloses from cellulosic biomass with water and heat to produce a cellulose-rich solids stream and a liquid extract comprising said water, wherein hemicelluloses and acetyl groups are released from said cellulosic biomass, and wherein said liquid extract contains at least 5 wt % solids;
   (b) hydrolyzing said liquid extract in the presence of sulfuric acid, heat, or enzymes, to produce a hydrolyzate comprising hemicellulose sugars and additional acetyl groups released during said hydrolyzing said liquid extract;
   (c) introducing said hydrolyzate to an evaporation stage, to produce a concentrated extract, wherein said evaporation stage is operated at a pH of 4.8 or less, wherein acetic acid obtained from said acetyl groups released from said cellulosic biomass and said additional acetyl groups released during said hydrolyzing said liquid extract, is evaporated from said evaporation stage, and wherein said concentrated extract comprises said hemicellulose sugars; and
   (d) recovering or further processing said hemicellulose sugars.

* * * * *